(12) United States Patent
Muller et al.

(10) Patent No.: US 9,498,642 B2
(45) Date of Patent: Nov. 22, 2016

(54) EYE THERAPY SYSTEM

(71) Applicant: Avedro, Inc., Waltham, MA (US)

(72) Inventors: David Muller, Boston, MA (US); John Marshall, Farnborough (GB); Marc D. Friedman, Needham, MA (US)

(73) Assignee: Avedro, Inc., Waltham, MA (US)

( * ) Notice: Subject to any disclaimer, the term of this patent is extended or adjusted under 35 U.S.C. 154(b) by 226 days.

(21) Appl. No.: 14/507,407

(22) Filed: Oct. 6, 2014

(65) Prior Publication Data
US 2015/0025440 A1 Jan. 22, 2015

Related U.S. Application Data

(63) Continuation of application No. 14/035,528, filed on Sep. 24, 2013, now Pat. No. 8,870,934, which is a continuation of application No. 12/909,228, filed on Oct. 21, 2010, now Pat. No. 8,574,277.

(60) Provisional application No. 61/253,736, filed on Oct. 21, 2009.

(51) Int. Cl.
*A61N 5/06* (2006.01)
*A61F 9/00* (2006.01)
(Continued)

(52) U.S. Cl.
CPC ............. *A61N 5/062* (2013.01); *A61F 9/0008* (2013.01); *A61K 31/14* (2013.01); *A61F 9/013* (2013.01)

(58) Field of Classification Search
CPC ....... A61N 5/062; A61F 9/008; A61F 9/013; A61K 31/14
See application file for complete search history.

(56) References Cited

U.S. PATENT DOCUMENTS

| 4,034,750 A | 7/1977 | Seiderman |
| 4,161,013 A | 7/1979 | Grodzinsky et al. |

(Continued)

FOREIGN PATENT DOCUMENTS

| DE | 10 2008 046834 | 3/2010 |
| EP | 1 561 440 | 8/2005 |

(Continued)

OTHER PUBLICATIONS

Abahussin, M. "3D Collagen Orientation Study of the Human Cornea Using X-ray Diffraction and Femtosecond Laser Technology" Investigative Ophthalmology & Visual Science, Nov. 2009, vol. 50, No. 11, pp. 5159-5164 (6 pages).

(Continued)

*Primary Examiner* — Gary Jackson
*Assistant Examiner* — Scott T Luan
(74) *Attorney, Agent, or Firm* — McDonnell Boehnen Hulbert & Berghoff LLP

(57) ABSTRACT

Embodiments apply a cross-linking agent to a region of corneal tissue. The cross-linking agent improves the ability of the corneal tissue to resist undesired structural changes. For example, the cross-linking agent may be Riboflavin or Rose Bengal, and the initiating element may be photoactivating light, such as ultraviolet (UV) light. In these embodiments, the photoactivating light initiates cross-linking activity by irradiating the applied cross-linking agent to release reactive oxygen radicals in the corneal tissue. The cross-linking agent acts as a sensitizer to convert $O_2$ into singlet oxygen which causes cross-linking within the corneal tissue. The rate of cross-linking in the cornea is related to the concentration of $O_2$ present when the cross-linking agent is irradiated with photoactivating light. Accordingly, the embodiments control the concentration of $O_2$ during irradiation to increase or decrease the rate of cross-linking and achieve a desired amount of cross-linking.

20 Claims, 7 Drawing Sheets

(51) Int. Cl.
*A61K 31/14* (2006.01)
*A61F 9/013* (2006.01)

(56) References Cited

U.S. PATENT DOCUMENTS

| | | | |
|---|---|---|---|
| 4,326,529 A | 4/1982 | Doss et al. |
| 4,381,007 A | 4/1983 | Doss |
| 4,665,913 A | 5/1987 | L'Esperance, Jr. |
| 4,712,543 A | 12/1987 | Baron |
| 4,764,007 A | 8/1988 | Task |
| 4,805,616 A | 2/1989 | Pao |
| 4,881,543 A | 11/1989 | Trembly et al. |
| 4,891,043 A | 1/1990 | Zeimer et al. |
| 4,969,912 A | 11/1990 | Kelman et al. |
| 4,994,058 A | 2/1991 | Raven et al. |
| 5,016,615 A | 5/1991 | Driller et al. |
| 5,019,074 A | 5/1991 | Muller |
| 5,103,005 A | 4/1992 | Gyure et al. |
| 5,171,254 A | 12/1992 | Sher |
| 5,171,318 A | 12/1992 | Gibson et al. |
| 5,281,211 A | 1/1994 | Parel et al. |
| 5,332,802 A | 7/1994 | Kelman et al. |
| 5,461,212 A | 10/1995 | Seiler et al. |
| 5,490,849 A | 2/1996 | Smith |
| 5,512,966 A | 4/1996 | Snook |
| 5,562,656 A | 10/1996 | Sumiya |
| 5,618,284 A | 4/1997 | Sand |
| 5,624,437 A | 4/1997 | Freeman et al. |
| 5,634,921 A | 6/1997 | Hood et al. |
| 5,766,171 A | 6/1998 | Silvestrini |
| 5,779,696 A | 7/1998 | Berry et al. |
| 5,786,893 A | 7/1998 | Fink et al. |
| 5,814,040 A | 9/1998 | Nelson et al. |
| 5,885,275 A | 3/1999 | Muller |
| 5,891,131 A | 4/1999 | Rajan et al. |
| 5,910,110 A | 6/1999 | Bastable |
| 6,033,396 A | 3/2000 | Huang et al. |
| 6,099,521 A | 8/2000 | Shadduck |
| 6,101,411 A | 8/2000 | Newsome |
| 6,104,959 A | 8/2000 | Spertell |
| 6,139,876 A | 10/2000 | Kolta |
| 6,161,544 A | 12/2000 | DeVore et al. |
| 6,162,210 A | 12/2000 | Shadduck |
| 6,188,500 B1 | 2/2001 | Rudeen et al. |
| 6,218,360 B1 | 4/2001 | Cintron et al. |
| 6,223,075 B1 | 4/2001 | Beck et al. |
| 6,270,221 B1 | 8/2001 | Liang et al. |
| 6,280,436 B1 | 8/2001 | Freeman et al. |
| 6,293,938 B1 | 9/2001 | Muller et al. |
| 6,319,273 B1 | 11/2001 | Chen et al. |
| 6,322,557 B1 | 11/2001 | Nikolaevich et al. |
| 6,325,792 B1 | 12/2001 | Swinger et al. |
| 6,334,074 B1 | 12/2001 | Spertell |
| 6,342,053 B1 | 1/2002 | Berry |
| 6,394,999 B1 | 5/2002 | Williams et al. |
| 6,402,739 B1 | 6/2002 | Neev |
| 6,413,255 B1 | 7/2002 | Stern |
| 6,478,792 B1 | 11/2002 | Hansel |
| 6,520,956 B1 | 2/2003 | Huang |
| 6,520,958 B1 | 2/2003 | Shimmick et al. |
| 6,537,545 B1 | 3/2003 | Karageozian et al. |
| 6,571,118 B1 | 5/2003 | Utzinger et al. |
| 6,572,849 B2 | 6/2003 | Shahinian, Jr. |
| 6,617,963 B1 | 9/2003 | Watters et al. |
| 6,673,067 B1 | 1/2004 | Peyman |
| 6,918,904 B1 | 7/2005 | Peyman |
| 6,946,440 B1 | 9/2005 | DeWoolfson et al. |
| 7,001,374 B2 | 2/2006 | Peyman |
| 7,004,902 B2 | 2/2006 | Luce |
| 7,044,945 B2 | 5/2006 | Sand |
| 7,073,510 B2 | 7/2006 | Redmond et al. |
| 7,130,835 B2 | 10/2006 | Cox et al. |
| 7,141,049 B2 | 11/2006 | Stern et al. |
| 7,192,429 B2 | 3/2007 | Trembly |
| 7,270,658 B2 | 9/2007 | Woloszko et al. |
| 7,331,350 B2 | 2/2008 | Kochevar et al. |
| 7,402,562 B2 | 7/2008 | DeWoolfson et al. |
| 7,753,943 B2 | 7/2010 | Strong |
| 7,898,656 B2 | 3/2011 | Yun et al. |
| 7,935,058 B2 | 5/2011 | Dupps et al. |
| 8,111,394 B1 | 2/2012 | Borysow et al. |
| 8,115,919 B2 | 2/2012 | Yun et al. |
| 8,366,689 B2 | 2/2013 | Marshall et al. |
| 8,414,911 B2 | 4/2013 | Mattson et al. |
| 8,475,437 B2 | 7/2013 | Mrochen et al. |
| 2001/0041856 A1 | 11/2001 | McDaniel |
| 2001/0055095 A1 | 12/2001 | D'Souza et al. |
| 2002/0002369 A1 | 1/2002 | Hood |
| 2002/0013577 A1 | 1/2002 | Frey et al. |
| 2002/0049437 A1 | 4/2002 | Silvestrini |
| 2002/0099363 A1 | 7/2002 | Woodward et al. |
| 2002/0159618 A1 | 10/2002 | Freeman et al. |
| 2002/0164379 A1 | 11/2002 | Nishihara et al. |
| 2003/0018255 A1 | 1/2003 | Martin et al. |
| 2003/0175259 A1 | 9/2003 | Karageozian et al. |
| 2003/0189689 A1 | 10/2003 | Rathjen |
| 2003/0216728 A1 | 11/2003 | Stern et al. |
| 2003/0231285 A1 | 12/2003 | Ferguson |
| 2004/0001821 A1 | 1/2004 | Silver et al. |
| 2004/0002694 A1 | 1/2004 | Pawlowski et al. |
| 2004/0071778 A1 | 4/2004 | Bellmann et al. |
| 2004/0093046 A1 | 5/2004 | Sand |
| 2004/0111086 A1 | 6/2004 | Trembly et al. |
| 2004/0143250 A1 | 7/2004 | Trembly |
| 2004/0199079 A1 | 10/2004 | Chuck et al. |
| 2004/0199158 A1 | 10/2004 | Hood et al. |
| 2004/0204707 A1 | 10/2004 | Hood et al. |
| 2004/0243160 A1 | 12/2004 | Shiuey et al. |
| 2005/0038471 A1 | 2/2005 | Chan et al. |
| 2005/0096515 A1 | 5/2005 | Geng |
| 2005/0149006 A1 | 7/2005 | Peyman |
| 2005/0271590 A1 | 12/2005 | Schwartz et al. |
| 2006/0135957 A1 | 6/2006 | Panescu |
| 2006/0149343 A1 | 7/2006 | Altshuler et al. |
| 2006/0177430 A1 | 8/2006 | Bhushan et al. |
| 2006/0189964 A1 | 8/2006 | Anderson et al. |
| 2006/0195076 A1 | 8/2006 | Blumenkranz et al. |
| 2006/0276777 A1 | 12/2006 | Coroneo |
| 2006/0287662 A1 | 12/2006 | Berry et al. |
| 2007/0024860 A1 | 2/2007 | Tobiason et al. |
| 2007/0027509 A1 | 2/2007 | Eisenberg et al. |
| 2007/0048340 A1 | 3/2007 | Ferren et al. |
| 2007/0055227 A1 | 3/2007 | Khalaj et al. |
| 2007/0074722 A1 | 4/2007 | Giroux et al. |
| 2007/0099966 A1 | 5/2007 | Fabricant |
| 2007/0123845 A1 | 5/2007 | Lubatschowski |
| 2007/0135805 A1 | 6/2007 | Peyman |
| 2007/0142828 A1 | 6/2007 | Peyman |
| 2007/0161976 A1 | 7/2007 | Trembly |
| 2007/0203547 A1 | 8/2007 | Costello et al. |
| 2007/0244470 A1 | 10/2007 | Barker et al. |
| 2007/0244496 A1 | 10/2007 | Hellenkamp |
| 2007/0265603 A1 | 11/2007 | Pinelli |
| 2008/0009901 A1 | 1/2008 | Redmond et al. |
| 2008/0015660 A1 | 1/2008 | Herekar |
| 2008/0027328 A1 | 1/2008 | Klopotek et al. |
| 2008/0063627 A1 | 3/2008 | Stucke et al. |
| 2008/0114283 A1 | 5/2008 | Mattson et al. |
| 2008/0139671 A1 | 6/2008 | Herekar |
| 2008/0208177 A1 | 8/2008 | Mrochen et al. |
| 2009/0024117 A1 | 1/2009 | Muller |
| 2009/0054879 A1 | 2/2009 | Berry |
| 2009/0069798 A1 | 3/2009 | Muller et al. |
| 2009/0116096 A1 | 5/2009 | Zalevsky et al. |
| 2009/0130176 A1 | 5/2009 | Bossy-Nobs et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0192437 A1 | 7/2009 | Soltz et al. |
| 2009/0209954 A1 | 8/2009 | Muller et al. |
| 2009/0234335 A1 | 9/2009 | Yee |
| 2009/0271155 A1 | 10/2009 | Dupps et al. |
| 2009/0275929 A1 | 11/2009 | Zickler |
| 2009/0276042 A1 | 11/2009 | Hughes et al. |

(56) References Cited

U.S. PATENT DOCUMENTS

| | | |
|---|---|---|
| 2010/0028407 A1 | 2/2010 | Del Priore et al. |
| 2010/0036488 A1 | 2/2010 | De Juan, Jr. et al. |
| 2010/0057060 A1 | 3/2010 | Herekar |
| 2010/0069894 A1 | 3/2010 | Mrochen et al. |
| 2010/0082018 A1 | 4/2010 | Panthakey |
| 2010/0094197 A1 | 4/2010 | Marshall et al. |
| 2010/0114109 A1 | 5/2010 | Peyman |
| 2010/0149487 A1 | 6/2010 | Ribak |
| 2010/0149842 A1 | 6/2010 | Muller et al. |
| 2010/0173019 A1 | 7/2010 | Paik et al. |
| 2010/0189817 A1 | 7/2010 | Krueger et al. |
| 2010/0191228 A1 | 7/2010 | Ruiz et al. |
| 2010/0203103 A1 | 8/2010 | Dana et al. |
| 2010/0204584 A1 | 8/2010 | Ornberg et al. |
| 2010/0210996 A1 | 8/2010 | Peyman |
| 2010/0286156 A1 | 11/2010 | Pinelli |
| 2010/0318017 A1 | 12/2010 | Lewis et al. |
| 2011/0077624 A1 | 3/2011 | Brady et al. |
| 2011/0098790 A1 | 4/2011 | Daxer |
| 2011/0118654 A1 | 5/2011 | Muller et al. |
| 2011/0152219 A1 | 6/2011 | Stagni et al. |
| 2011/0190742 A1 | 8/2011 | Anisimov |
| 2011/0202114 A1 | 8/2011 | Kessel et al. |
| 2011/0208300 A1 | 8/2011 | de Juan, Jr. et al. |
| 2011/0237999 A1 | 9/2011 | Muller et al. |
| 2011/0264082 A1 | 10/2011 | Mrochen et al. |
| 2011/0288466 A1 | 11/2011 | Muller et al. |
| 2011/0301524 A1 | 12/2011 | Bueler et al. |
| 2012/0083772 A1 | 4/2012 | Rubinfeld et al. |
| 2012/0203051 A1 | 8/2012 | Brooks et al. |
| 2012/0203161 A1 | 8/2012 | Herekar |
| 2012/0215155 A1 | 8/2012 | Muller et al. |
| 2012/0283621 A1 | 11/2012 | Muller et al. |
| 2012/0289886 A1 | 11/2012 | Muller et al. |
| 2012/0302862 A1 | 11/2012 | Yun et al. |
| 2012/0303008 A1 | 11/2012 | Muller et al. |
| 2012/0310083 A1 | 12/2012 | Friedman et al. |
| 2012/0310223 A1 | 12/2012 | Knox et al. |
| 2013/0060187 A1 | 3/2013 | Friedman et al. |
| 2013/0085370 A1 | 4/2013 | Friedman et al. |
| 2013/0116757 A1 | 5/2013 | Russmann |
| 2014/0194957 A1 | 7/2014 | Rubinfeld et al. |
| 2014/0249509 A1 | 9/2014 | Rubinfeld et al. |

FOREIGN PATENT DOCUMENTS

| | | |
|---|---|---|
| EP | 1 790 383 | 5/2007 |
| EP | 2 253 321 | 11/2010 |
| EP | 2 490 621 | 8/2012 |
| IT | MI2010A001236 | 5/2010 |
| KG | 1376 | 8/2011 |
| RU | 2086215 | 8/1997 |
| RU | 2098057 | 12/1997 |
| RU | 2121825 | 11/1998 |
| RU | 2127099 | 3/1999 |
| RU | 2127100 | 3/1999 |
| RU | 2309713 | 11/2007 |
| RU | 2359716 | 6/2009 |
| RU | 2420330 | 6/2011 |
| RU | 2428152 | 9/2011 |
| RU | 2456971 | 7/2012 |
| WO | WO 00/74648 | 12/2000 |
| WO | WO 01/58495 | 8/2001 |
| WO | WO 2004/052223 | 6/2004 |
| WO | WO 2005/110397 | 11/2005 |
| WO | WO 2006/012947 | 2/2006 |
| WO | WO 2006/128038 | 11/2006 |
| WO | WO 2007/001926 | 1/2007 |
| WO | WO 2007/053826 | 5/2007 |
| WO | WO 2007/081750 | 7/2007 |
| WO | WO 2007/120457 | 10/2007 |
| WO | WO 2007/139927 | 12/2007 |
| WO | WO 2007/143111 | 12/2007 |
| WO | WO 2008/000478 | 1/2008 |
| WO | WO 2008/052081 | 5/2008 |
| WO | WO 2008/095075 | 8/2008 |
| WO | WO 2009/073213 | 6/2009 |
| WO | WO 2009/114513 | 9/2009 |
| WO | WO 2009/146151 | 12/2009 |
| WO | WO 2010/011119 | 1/2010 |
| WO | WO 2010/015255 | 2/2010 |
| WO | WO 2010/023705 | 3/2010 |
| WO | WO 2010/093908 | 8/2010 |
| WO | WO 2011/019940 | 2/2011 |
| WO | WO 2011/116306 | 9/2011 |
| WO | WO 2012/004726 | 1/2012 |
| WO | WO 2012/047307 | 4/2012 |
| WO | WO 2012/149570 | 11/2012 |
| WO | WO 2012/174453 | 12/2012 |
| WO | WO 2013/148713 | 10/2013 |
| WO | WO 2013/148895 | 10/2013 |
| WO | WO 2013/148896 | 10/2013 |
| WO | WO 2013/149075 | 10/2013 |
| WO | WO 2014/202736 | 12/2014 |

OTHER PUBLICATIONS

Barbarino, S. et al., "Post-LASIK ectasia: Stabilization and Effective Management with Riboflavin / ultraviolet A-induced collagen cross-linking," Association for Research in Vision and Ophthalmology, 2006 (1 page).

Burke, JM et al., Abstract for "Retinal proliferation in response to vitreous hemoglobin or iron", Investigative Ophthalmology & Visual Science, May 1981, 20(5), pp. 582-592 (1 page).

Chace, KV. et al., Abstract for "The role of nonenzymatic glycosylation, transition metals, and free radicals in the formation of collagen aggregates", Arch Biochem Biophys., Aug. 1, 1991, 288(2), pp. 473-80 (1 page).

Friedman, M. et al. "Advanced Corneal Cross-Linking System with Fluorescence Dosimetry", Journal of Ophthalmology, vol. 2012, Article ID 303459, dated May 7, 2012 (6 pages).

Kanellopoulos, A. J., "Collagen Cross-linking in Early Keratoconus With Riboflavin in a Femtosecond Laser-created Pocket: Initial Clinical Results", Journal of Refractive Surgery, Aug. 18, 2009.

Kanellopoulos, A. J., "Keratoconus management: UVA-induced collagen cross-linking followed by a limited topo-guided surface excimer ablation," American Academy of Ophthalmology, 2006 (25 pages).

Kanellopoulos, A. J., "Ultraviolet A cornea collagen cross-linking, as a pre-treatment for surface excimer ablation in the management of keratoconus and post-LASIK ectasia," American Academy of Ophthalmology, 2005 (28 pages).

Meek, K.M. et al. "The Cornea and Sclera", Collagen: Structure and Mechanics, Chapter 13, pp. 359-396, 2008 (38 pages).

Pinelli, R., "Panel Discussion: Epithelium On/Off, Corneal abrasion for CCL contra", presented at the 3° International Congress of Corneal Cross Linking on Dec. 7-8, 2007 in Zurich (36 pages).

Pinelli R., "Resultados de la Sociedad de Cirugia Refractiva Italiana (SICR) utilizando el C3-R" presented at the Istitutor Laser Microchirurgia Oculare in 2007 in Italy (23 pages).

Pinelli R., "The Italian Refractive Surgery Society (SICR) results using C3-R" presented Jun. 22-23, 2007 in Italy (13 pages).

Randall, J. et al., "The Measurementand Intrepretation of Brillouin Scattering in the Lens of the Eye," The Royal Society, Abstract only, published 2013 [available online at http://rspb.royalsocietypublishing.org/content/214/1197/449.short] (1 page).

Reiss, S. et al., "Non-Invasive, ortsaufgeloeste Bestimmung von Gewebeeigenschaften derAugenlinse, Dichte undProteinkonzentration unter Anwendung der Brillouin-spektroskopie", Klin Monatsbl Augenheilkd, vol. 228, No. 12, pp. 1079-1085, Dec. 13, 2011 (7 pages).

Reiss, S. et al., "Spatially resolved Brillouin Spectroscopy to determine the rheological properties of the eye lens", Biomedical Optics Express, vol. 2, No. 8, p. 2144, Aug. 1, 2011 (1 page).

Scarcelli, G. et al., "Brillouin Optical Microscopy for Corneal Biomechanics", Investigative Ophthalmology & Visual Science, Jan. 2012, vol. 53, No. 1, pp. 185-190 (6 pages).

(56) References Cited

OTHER PUBLICATIONS

Sun, G.J. et al., Abstract for "Properties of 2,3-butanedione and 1-phenyl-1,2-propanedione as new photosensitizers for visible light cured dental resin composites", Polymer 41, pp. 6205-6212, published in 2000 (1 page).

Tomlinson, A. "Tear Film Osmolarity: Determination of a Referent for Dry Eye Diagnosis", Investigative Ophthalmology & Visual Science, Oct. 2006, vol. 47, No. 10, pp. 4309-4315 (7 pages).

Wong, J. et al., "Post-Lasik ectasia: PRK following previous stablization and effective management with Riboflavin / ultraviolet A-induced collagen cross-linking," Association for Research in Vision and Ophthalmology, 2006 (1 page).

Acosta A. et al., "Corneal Stroma Regeneration in Felines After Supradescemetic Keratoprothesis Implantation," *Cornea*, vol. 25, No. 7, pp. 830-838; Aug. 2006 (9 pages).

Averianova, O. S., "Nastoyaschee I buduschee kross-linkage." Mir Ofalmologii, 2010, [online] [retrieved on Feb. 13, 2014] Retrieved from the internet: http://miroft.org.ua/publications/.html (3 pages).

Baier J. et al., "Singlet Oxygen Generation by UVA Light Exposure of Endogenous Photosensitizers," *Biophysical Journal*, vol. 91(4), pp. 1452-1459; Aug. 15, 2006 (8 pages).

Ballou, D. et al., "Direct Demonstration of Superoxide Anion Production During the Oxidation of Reduced Flavin and of Its Catalytic Decomposition by Erythrocuprein," Biochemical and Biophysical Research Communications vol. 36, No. 6, pp. 898-904, Jul. 11, 1969 (7 pages).

Berjano E., et al., "Radio-Frequency Heating of the Cornea: Theoretical Model and In Vitro Experiments," *IEEE Transactions on Biomedical Engineering*, vol. 49, No. 3, pp. 196-205; Mar. 2002 (10 pages).

Berjano E., et al., "Ring Electrode for Radio-frequency Heating of the Cornea: Modelling and in vitro Experiments," *Medical & Biological Engineering & Computing*, vol. 41, pp. 630-639; Jun. 2003 (10 pages).

Brüel, A., "Changes in Biomechanical Properties, Composition of Collagen and Elastin, and Advanced Glycation Endproducts of the Rat Aorta in Relation to Age," Atherosclerosis 127, Mar. 14, 1996 (11 pages).

Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238 (8 pages).

Chan B.P., et al., "Effects of photochemical crosslinking on the microstructure of collagen and a feasibility study on controlled protein release;" *Acta Biomaterialia*, vol. 4, Issue 6, pp. 1627-1636; Jul. 1, 2008 (10 pages).

Chandonnet, "$CO_2$ Laser Annular Thermokeratoplasty: A Preliminary Study," *Lasers in Surgery and Medicine*, vol. 12, pp. 264-273; 1992 (10 pages).

Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011 (3 pages).

Corbett M., et al., "Effect of Collagenase Inhibitors on Corneal Haze after PRK," *Exp. Eye Res.*, vol. 72, Issue 3, pp. 253-259; Jan. 2001 (7 pages).

Coskenseven E. et al., "Comparative Study of Corneal Collagen Cross-linking With Riboflavin and UVA Irradiation in Patients With Keratoconus," *Journal of Refractive Surgery*, vol. 25, issue 4, pp. 371-376; Apr. 2009 (6 pages).

"DEFINITY (perflutren) injection, suspension [Bristol-Myers Squibb Medical Imaging]," http://dailymed.nlm.nih.gov/dailymed/drugInfo.cfm?id=8338, revised Sep. 2008, retrieved via the internet archive from http://web.archive.org/web/20100321105500/http://dailymed.nlm.nih.gov/dailymed/drugInfo.cfm?id=8338, on Dec. 14, 2011 (15 pages).

Ehlers W., et al., "Factors Affecting Therapeutic Concentration of Topical Aminocaproic Acid in Traumatic Hyphema," *Investigative Ophthalmology & Visual Science*, vol. 31, No. 11, pp. 2389-2394; Nov. 1990 (6 pages).

Erskine H., "Avedro Becomes Sponsor of US FDA Clinical Trials of Corneal Collagen Crosslinking," Press Release, Mar. 16, 2010 (1 page).

Fite et al., "Noninvasive Multimodal Evaluation of Bioengineered Cartilage Constructs Combining Time-Resolved Fluorescence and Ultrasound Imaging." Tissue Eng: Part C vol. 17, No. 4, 2011 (10 pages).

Frucht-Pery, et al. "Iontophoresis—gentamicin delivery into the rabbit cornea, using a hydrogel delivery probe," Jun. 20, 2003 (5 pages).

Gibson, Q. et al., "The Oxidation of Reduced Flavin Mononucleotide by Molecular Oxygen," Biochem. J. (1962) 83, 368-377 (10 pages).

Givens et al. "A Photoactivated Diazpryruvoyl Cross-Linking Agent for Bonding Tissue Containing Type-I Collagen." Photochemistry and Photobiology. vol. 78, No. 1, 2003 (pp. 23-29).

Glenn J.V., et al., "Advanced Glycation End Product (AGE) Accumulation on Bruch's Membrane: Links to Age-Related RPE Dysfunction;" *Investigative Ophthalmology & Visual Science*, vol. 50, No. 1, pp. 441-451; Jan. 2009 (11 pages).

Gravitz L., "Laser Show in the Surgical Suite: Lasers and a century-old dye could supplant needles and thread;" *technology review*, MIT, Mar./Apr. 2009; retrieved from http://www.technologyreview.com/biomedicine/22088/?nlid=1767, on Sep. 26, 2011 (2 pages).

Hafezi F., et al., "Collagen Crosslinking with Ultraviolet-A and Hypoosmolar Riboflavin Solution in Thin Corneas," *J. Catract Refract. Surg.*, vol. 35, No. 1, pp. 621-624; Apr. 2009 (4 pages).

Hitzenberger et al., "Birefringence Properties of the Human Cornea Measured With Polarization Sensitive Optical Coherence Tomography," Bull. Soc. Beige Ophtalmol., 302, 153-168, 2006 (16 pages).

Holmström, B. et al., "Riboflavin as an Electron Donor in Photochemical Reactions," 1867-1871, Nov. 29, 1960 (5 pages).

How to Use DEFINITY: "Frequently Asked Questions;" retrieved from http://www.definityimaging.com/how-faq.html, on Sep. 26, 2011 (3 pages) (date unknown, prior to Apr. 26, 2010).

IMEX, "KXL System: Crosslinking Para Cirugia Corneal Bibliografia Cientifica," Product Literature, Nov. 23, 2010 (24 pages).

Kamaev et al., "Photochemical Kinetics of Corneal Cross-Linking With Riboflavin," Investigative Ophthalmology & Visual Science, Apr. 2012, vol. 53, No. 4, pp. 2360-2367 (8 pages).

Kampik D. et al., "Influence of Corneal Collagen Crosslinking With Riboflavin and Ultraviolet-A Irradiation on Excimer Laser Surgery," *Investigative Ophthalmology & Visual Science*, vol. 51, No. 8, pp. 3929-3934; Aug. 2010 (6 pages).

Kissner Anja, et al., "Pharmacological Modification of the Epithelial Permeability by Benzalkonium Chloride in UVA/Riboflavin Corneal Collagen Cross-Linking," *Current Eye Research* 35(8), pp. 715-721; Mar. 2010 (7 pages).

Koller, T. et. Al., "Complication and failure rates after corneal crosslinking," *Journal Cataract and refractive surgery*, vol. 35, No. 8, Aug. 2009, pp. 1358-1362.

Koller T., et al., "Therapeutische Quervernetzung der Hornhaut mittels UVA and Riboflavin: Therapeutic Cross-Linking of the Cornea Using Riboflavin/UVA," *Klinische Monatsblätter für Augenheilkunde*, vol. 224, No. 9, pp. 700-706; Sep. 2007 (7 pages).

Kornilovsky, I. M. "Novye neinvazivnye tekhnologii lazernoy modifikatsii optiko-refraksionnykk struktur glaza. Refraktsionnaya khirurgiya I oftalmologiya." vol. 9, No. 3, 2006 (pp. 17-26).

Krueger, Ronald R., "Rapid VS Standard Collagen CXL with Equivalent Energy Dosing," presentation slides; available at http://www.slideshare.net/Iogen/krueger-herekar-rapid-cross-linking (date unknown, prior to Nov. 9, 2009) (26 pages).

Massey, V., "Activation of Molecular Oxygen by Flavins and Flavoproteins," The Journal of Biological Chemistry vol. 269, No. 36, Issue of Sep. 9, pp. 22459-22462, 1994 (4 pages).

Marzouky, et. al., Tensioactive-mediated Transepithelial Corneal Cross-linking—First Laboratory Report, European Ophthalmic Review, 2009, 3(2), pp. 67-70.

(56) References Cited

OTHER PUBLICATIONS

Li, C. et al. "Elastic Properties of Soft Tissue-Mimicking Phantoms Assessed by Combined Use of Laser Ultrasonics and Low Coherence Interferometry." Optics Express. vol. 19, No. 11, May 9, 2011 (pp. 10153-10163).

Li, C. et al. "Noncontact All-Optical Measurement of Corneal Elasticity." Optics Letters. vol. 37, No. 10, May 15, 2012 (pp. 1625-1627).

Li, P. et al. "In Vivo Microstructural and Microvascular Imaging of the Human Corneo-Scleral Limbus Using Optical Coherence Tomography." Biomedical Optics Express. vol. 2, No. 11, Oct. 18, 2011 (pp. 3109-3118).

Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 pages).

Muller L., et al., "The Specific Architecture of the Anterior Stroma Accounts for Maintenance of Corneal Curvature," *Br. J. Opthalmol.*, vol. 85, pp. 437-443; Apr. 2001 (8 pages).

Mulroy L., et al., "Photochemical Keratodesmos for repair of Lamellar corneal Incisions;" Investigative Ophthalmology & Visual Science, vol. 41, No. 11, pp. 3335-3340; Oct. 2000 (6 pages).

Naoumidi T., et al., "Two-Year Follow-up of Conductive Keratoplasty for the Treatment of Hyperopic Astigmatism," *J. Cataract Refract. Surg.*, vol. 32(5), pp. 732-741; May 2006 (10 pages).

Nesterov, A. P. "Transpalpebralny Tonometr Dlya Izmereniya Vnutriglaznogo Davleniya." Feb. 2, 2006. [online] [Retrieved Dec. 17, 2012] Retrieved from the Internet: <URL: http://grpz.ru/images/publication_pdf/27.pdf>.

O'Neil A.C., et al., "Microvascular Anastomosis Using a Photochemical Tissue Bonding Technique;" Lasers in Surgery and Medicine, vol. 39, Issue 9, pp. 716-722; Oct. 2007 (7 pages).

O.V. Shilenskaya et al., "Vtorichnaya katarakta posle implantatsii myagkikh IOL," [online] Aug. 21, 2008 [retrieved Apr. 3, 2013] Retrieved from the Internet: <URL:http://www.reper.ru/rus/index.php?catid=210> (4 pages).

Paddock C., Medical News Today: "Metastatic Melanoma PV-10 Trial Results Encouraging Says Drug Company;" Jun. 9, 2009; retrieved from http://www.medicalnewstoday.com/articles/153024.php, on Sep. 26, 2011 (2 pages).

Pallikaris I., et al., "Long-term Results of Conductive Keratoplasty for low to Moderate Hyperopia," *J. Cataract Refract. Surg.*, vol. 31(8), pp. 1520-1529; Aug. 2005 (10 pages).

Pinelli, R. "Corneal Cross-Linking with Riboflavin: Entering a New Era in Ophthalmology." Ophthalmology Times Europe. vol. 2, No. 7, Sep. 1, 2006, [online], [retrieved on May 20, 2013]. Retrieved from the Internet: <URL: http://www.oteurope.com/ophthalmologytimeseurope/Cornea/Corneal-cross-linking-with-riboflavin-entering-a-n/ArticleStandard/Article/detail/368411> (3 pages).

Pinelli R., et al., "C3-Riboflavin Treatments: Where Did We Come From? Where Are We Now?" *Cataract & Refractive Surgery Today Europe*, Summer 2007, pp. 36-46; Jun. 2007 (10 pages).

Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," *J. Cataract Refract. Surgery*, vol. 35, No. 6, pp. 1055-1062; Jun. 2009 (8 pages).

Proano C.E., et al., "Photochemical Keratodesmos for Bonding Corneal Incisions;" *Investigative Ophthalmology & Visual Science*, vol. 45, No. 7, pp. 2177-2181; Jul. 2004 (5 pages).

Reinstein, D. Z. et al. "Epithelial Thickness Profile as a Method to Evaluate the Effectiveness of Collagen Cross-Linking Treatment After Corneal Ectasis." Journal of Refractive Surgery. vol. 27, No. 5, May 2011 (pp. 356-363). [Abstract only].

Rocha K., et al., "Comparative Study of Riboflavin-UVA Crosslinking and "Flash-linking" Using Surface Wave Elastometry," *Journal of Refractive Surgery*, vol. 24 Issue 7, pp. S748-S751; Sep. 2008 (4 pages).

Rolandi et al., "Correlation of Collagen-Linked Fluorescence and Tendon Fiber Breaking Time." Gerontology 1991;27:240-243 (4 pages).

RxList: "Definity Drug Description;" *The Internet Drug Index*, revised Jun. 16, 2008, retrieved from http://www.rxlist.com/definity-drug.htm, on Sep. 26, 2011 (4 pages).

Sheehan M., et al., "Illumination System for Corneal Collagen Crosslinking," *Optometry and Vision Science*, vol. 88, No. 4, pp. 512-524; Apr. 2011 (13 pages).

Shell, J., "Pharmacokinetics of Topically Applied Ophthalmic Drugs," *Survey of Ophthalmology*, vol. 26, No. 4, pp. 207-218; Jan.-Feb. 1982 (12 pages).

Song P., Metzler D. "Photochemical Degradation of Flavins—IV. Studies of the Anaerobic Photolysis of Riboflavin." Photochemistry and Photobiology, vol. 6, pp. 691-709, 1967 (21 pages).

Sonoda S., "Gene Transfer to Corneal Epithelium and Keratocytes Mediated by Ultrasound with Microbubbles," *Investigative Ophthalmology & Visual Science*, vol. 47, No. 2, pp. 558-564; Feb. 2006 (7 pages).

Spoerl E., et al., "Artificial Stiffening of the Cornea by Induction of Intrastromal Cross-links," *Der Ophthalmologe*, vol. 94, No. 12, pp. 902-906; Dec. 1997 (5 pages).

Spoerl E., et al., "Induction of Cross-links in Corneal Tissue," *Experimental Eye Research*, vol. 66, Issue 1, pp. 97-103; Jan. 1998 (7 pages).

Spoerl E. et al., "Safety of UVA-Riboflavin Cross-Linking of the Cornea," *Cornea*, vol. 26, No. 4, pp. 385-389; May 2007 (5 pages).

Spoerl E., et al., "Techniques for Stiffening the Cornea," *Journal of Refractive Surgery*, vol. 15, Issue 6, pp. 711-713; Nov.-Dec. 1999 (4 pages).

Tessier FJ, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).

Thornton, I. et. al., "Biomechancial Effects of Intraocular Pressure Elevation on Optic Berve/Lamina Cribrosa before and after Peripapillary Scleral Collagen Cross-Linking." Invest. Ophthalm,ol. Vis. Sci., Mar. 2009, 50(3): pp. 1227-1233.

Trembly et al., "Microwave Thermal Keratoplasty for Myopia: Keratoscopic Evaluation in Porcine Eyes," *Journal of Refractive Surgery*, vol. 17, No. 6, pp. 682-688; Nov./Dec. 2001 (8 pages).

Turgunbaev N.A. et al. Fotomodifikatsiya sklery u bolnykh s progressiruyuschei blizorukostyu (predvaritelnoe soobschenie). 2010 [online]. Retrieved from the Internet:<URL: http://www.eyepress.ru/article.aspx?7484> (2 pages).

"UV-X: Radiation System for Treatment of Keratokonus," *PESCHKE Meditrade GmbH;* retrieved from http://www.peschkemed.ch/ on Sep. 27, 2011 (date unknown, prior to Sep. 16, 2008) (1 page).

Vasan S., et al., "An agent cleaving glucose-derived protein crosslinks in vitro and in vivo;" *Letters to Nature*, vol. 382, pp. 275-278; Jul. 18, 1996 (4 pages).

Verzijl et al. Crosslinking by Advanced Glycation End Products Increases the Stiffness of the Collagen Network in Human Articular Cartilage. Arthritis & Rheumatism vol. 46, No. 1, Jan. 2002, pp. 114-123 (10 pages).

Wollensak G., et al., "Biomechanical and Histological Changes After Corneal Crosslinking With and Without Epithelial Debridement," *J. Cataract Refract. Surg.*, vol. 35, Issue 3, pp. 540-546; Mar. 2009 (7 pages).

Wollensak G., et al., "Collagen Crosslinking of Human and Porcine Sclera," *J. Cataract Refract. Surg.*, vol. 30, Issue 3, pp. 689-695; Mar. 2004 (7 pages).

Wollensak G., et al., "Cross-linking of Scleral Collagen in the Rabbit Using Riboflavin and UVA," *Acta Ophtalmologica Scandinavica*, vol. 83(4), pp. 477-482; Aug. 2005 (6 pages).

Wollensak G., "Crosslinking Treatment of Progressive Keratoconus: New Hope," *Current Opinion in Ophthalmology*, vol. 17(4), pp. 356-360; Aug. 2006 (5 pages).

Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).

(56) References Cited

OTHER PUBLICATIONS

Wollensak G., et al., "Riboflavin/Ultraviolet-A-induced Collagen Crosslinking for the Treatment of Keratoconus," *American Journal of Ophthalmology*, vol. 135, No. 5, pp. 620-627; May 2003 (8 pages).

Wollensak, G. et al. "Laboratory Science: Stress-Strain Measurements of Human and Porcine Corneas after Riboflavin-Ultraviolet-A-Induced Cross-Linking." Journal of Cataract and Refractive Surgery. vol. 29, No. 9, Sep. 2003 (pp. 1780-1785).

Yang H., et al., "3-D Histomorphometry of the Normal and Early Glaucomatous Monkey Optic Nerve Head: Lamina Cribrosa and Peripapillary Scleral Position and Thickness," *Investigative Ophthalmology & Visual Science*, vol. 48, No. 10, pp. 4597-4607; Oct. 2007 (11 pages).

Yang N., Oster G. Dye-sensitized photopolymerization in the presence of reversible oxygen carriers. J. Phys. Chem. 74, 856-860 (1970) (5 pages).

Zhang, Y. et al., "Effect of the Synthetic NC-1059 Peptide on Diffusion of Riboflavin Across an Intact Corneal Epithelium", May 6, 2012, ARBO 2012 Annual Meeting Abstract, 140 Stroma and Keratocytes, program number: 1073, poster board number: A109.

Zhang, Y. et al., "Effects of Ultraviolet-A and Riboflavin on the Interaction of Collagen and Proteoglycans during Corneal Crosslinking", Journal of Biological Chemistry, vol. 286, No. 15, dated Apr. 15, 2011 (pp. 13011-13022).

Zderic V., et al., "Drug Delivery Into the Eye With the Use of Ultrasound," *J. Ultrasound Med*, vol. 23(10), pp. 1349-1359; Oct. 2004 (11 pages).

Zderic V., et al., "Ultrasound-enhanced Transcorneal Drug Delivery," *Cornea* vol. 23, No. 8, pp. 804-811; Nov. 2004 (8 pages).

International Search Report and Written Opinion mailed Feb. 6, 2014 which issued in International Patent Application No. PCT/US2013/068588 (6 pages).

International Search Report and Written Opinion mailed Dec. 21, 2013 which issued in International Patent Application No. PCT/US2010/053551 (13 pages).

International Search Report and Written Opinion mailed Jul. 18, 2013 which issued in International Patent Application No. PCT/US2013/032567 (6 pages).

International Search Report and Written Opinion mailed Apr. 11, 2013 which issued in International Patent Application No. PCT/US2012/062843 (8 pages).

EYE THERAPY SYSTEM

CROSS REFERENCE TO RELATED APPLICATIONS

This application is a continuation of U.S. patent application Ser. No. 14/035,528, filed Sep. 24, 2013, which is a continuation of U.S. Pat. No. 8,574,277, filed Oct. 21, 2010, which claims priority to U.S. Provisional Application No. 61/253,736, filed Oct. 21, 2009, the contents of these applications being incorporated entirely herein by reference.

BACKGROUND OF THE INVENTION

1. Field of the Invention

The invention pertains to the field of conducting eye therapy, and more particularly, to systems and methods for stabilizing changes to corneal tissue as a part of eye therapy.

2. Description of Related Art

A variety of eye disorders, such as myopia, keratoconus, and hyperopia, involve abnormal shaping of the cornea. Laser-assisted in-situ keratomileusis (LASIK) is one of a number of corrective procedures that reshape the cornea so that light traveling through the cornea is properly focused onto the retina located in the back of the eye. During LASIK eye surgery, an instrument called a microkeratome is used to cut a thin flap in the cornea. The corneal flap is then peeled back and the underlying corneal tissue is ablated to the desired shape with an excimer laser. After the desired reshaping of the cornea is achieved, the corneal flap is put back in place and the surgery is complete.

In another corrective procedure that reshapes the cornea, thermokeratoplasty provides a noninvasive procedure that applies electrical energy in the microwave or radio frequency (RF) band to the cornea. In particular, the electrical energy raises the corneal temperature until the collagen fibers in the cornea shrink at about 60° C. The onset of shrinkage is rapid, and stresses resulting from this shrinkage reshape the corneal surface. Thus, application of energy according to particular patterns, including, but not limited to, circular or annular patterns, causes aspects of the cornea to flatten and improves vision in the eye.

The success of procedures, such as LASIK or thermokeratoplasty, in addressing eye disorders, such as myopia, keratoconus, and hyperopia, depends on whether the desired reshaping of the cornea has been sufficiently stabilized.

SUMMARY OF THE INVENTION

Embodiments according to aspects of the present invention provide systems and methods for stabilizing corneal tissue and improving its biomechanical strength. For example, the embodiments may be employed to preserve the desired reshaping of corneal tissue produced by eye therapies, such as thermokeratoplasty or LASIK surgery.

In particular, the embodiments apply a cross-linking agent to a region of corneal tissue. The cross-linking agent improves the ability of the corneal tissue to resist undesired structural changes. For example, the cross-linking agent may be Riboflavin or Rose Bengal, and the initiating element may be photoactivating light, such as ultraviolet (UV) light. In these embodiments, the photoactivating light initiates cross-linking activity by irradiating the applied cross-linking agent to release reactive oxygen radicals in the corneal tissue. The cross-linking agent, e.g. Riboflavin or Rose Bengal, acts as a sensitizer to convert $O_2$ into singlet oxygen which causes cross-linking within the corneal tissue.

The rate of cross-linking in the cornea is related to the concentration of $O_2$ present when the cross-linking agent is irradiated with photoactivating light. Accordingly, aspects of the present invention control the concentration of $O_2$ during irradiation to increase or decrease the rate of cross-linking and achieve a desired amount of cross-linking.

To increase the presence of $O_2$ during irradiation, the cross-linking agent in some embodiments may be saturated or supersaturated with $O_2$ before application to the cornea.

In other embodiments, a steady state of $O_2$ may be maintained above the eye to expose the cornea to higher concentrations of $O_2$ during irradiation.

In further embodiments, a gel, such as a methylcellulose gel, may be saturated or supersaturated with $O_2$. The gel acts as a carrier for $O_2$. The gel may then be applied to the cornea after the cross-linking agent has been applied to the cornea. Alternatively, the gel may be mixed with the cross-linking agent before the cross-linking agent is applied to the cornea.

In some embodiments, the rate of cross-linking may be monitored in real time and the concentration of $O_2$ may be dynamically increased or decreased to achieve a desired amount of cross-linking. Thus, embodiments include a system that provides a first amount of $O_2$ above the eye to introduce $O_2$ to the corneal tissue and expose the cornea to a first concentration of $O_2$ during irradiation. Based on the feedback from the real time monitoring, the system can then provide a second amount of $O_2$ above the eye to introduce another amount of $O_2$ to the corneal tissue and expose the cornea to a second concentration of $O_2$ during irradiation. The first amount of $O_2$ may be greater than the second amount of $O_2$, or vice versa. Changing the cornea's exposure from the first concentration to the second concentration changes the rate of cross-linking in the corneal tissue. Further changes to the concentration of $O_2$ during irradiation may be effected to control the rate of cross-linking. When necessary, the amount of $O_2$ above the eye may be substantially reduced to zero to prevent further introduction of $O_2$ to the corneal tissue during irradiation.

Other aspects, features, and advantages of the present invention are readily apparent from the following detailed description, by illustrating a number of exemplary embodiments and implementations, including the best mode contemplated for carrying out the present invention. The present invention is also capable of other and different embodiments, and its several details can be modified in various respects, all without departing from the spirit and scope of the present invention. Accordingly, the drawings and descriptions are to be regarded as illustrative in nature, and not as restrictive. The invention is to cover all modifications, equivalents, and alternatives falling within the spirit and scope of the invention.

DETAILED DESCRIPTION

Embodiments according to aspects of the present invention provide systems and methods for stabilizing corneal tissue and improving its biomechanical strength. For example, the embodiments may be employed to preserve the desired reshaping of corneal tissue produced by eye therapies, such as thermokeratoplasty or LASIK surgery.

Figure 1A:
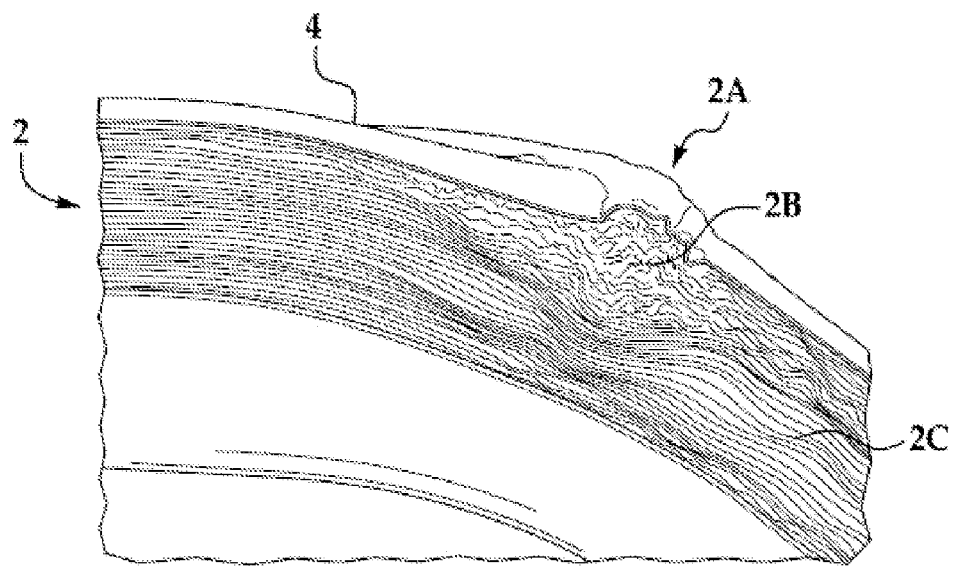
FIG. 1A illustrates a high resolution image of a cornea after energy has been applied.
Figure 1B:
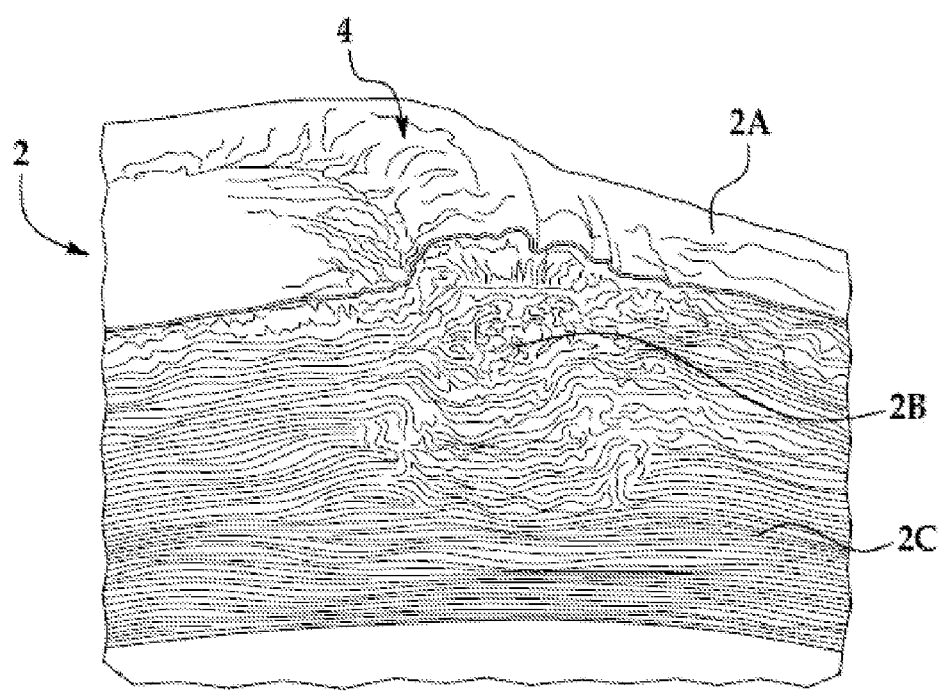
FIG. 1B illustrates another high resolution images of the cornea of FIG. 1A.

FIGS. 1A-D illustrate an example of the effect of applying heat to corneal tissue with thermokeratoplasty. In particular, FIGS. 1A and 1B illustrate high resolution images of cornea 2 after heat has been applied. As FIGS. 1A and 1B show, a lesion 4 extends from the corneal surface 2A to a mid-depth region 2B in the corneal stroma 2C. The lesion 4 is the result of changes in corneal structure induced by the application of heat as described above. These changes in structure result in an overall reshaping of the cornea 2. It is noted that the application of heat, however, has not resulted in any heat-related damage to the corneal tissue.

Figure 1C:
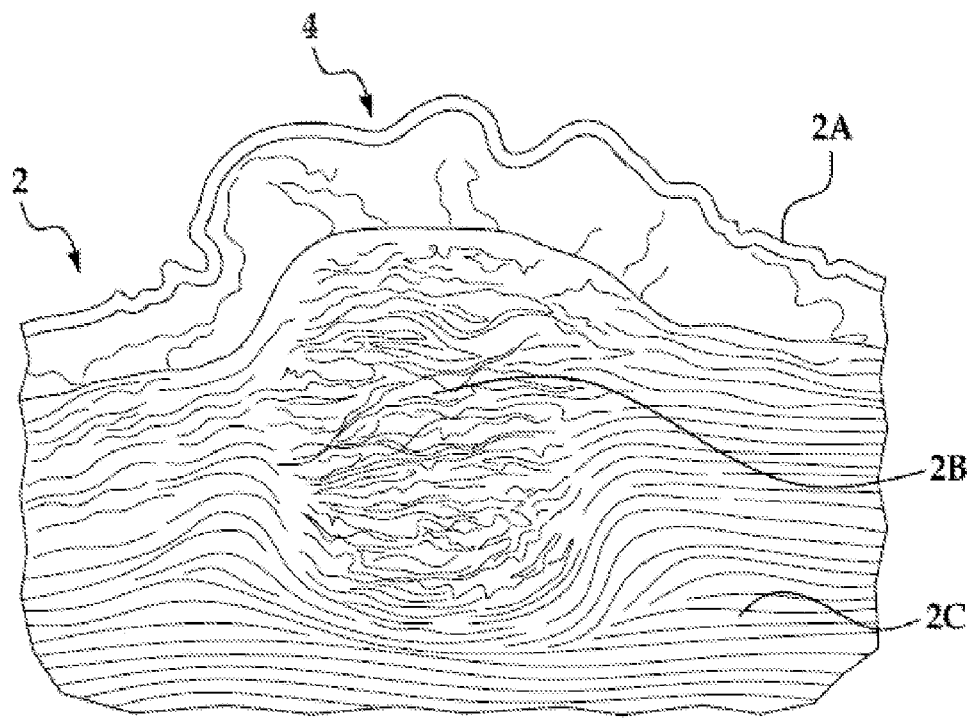
FIG. 1C illustrates a histology image of the cornea of FIG. 1A.
Figure 1D:
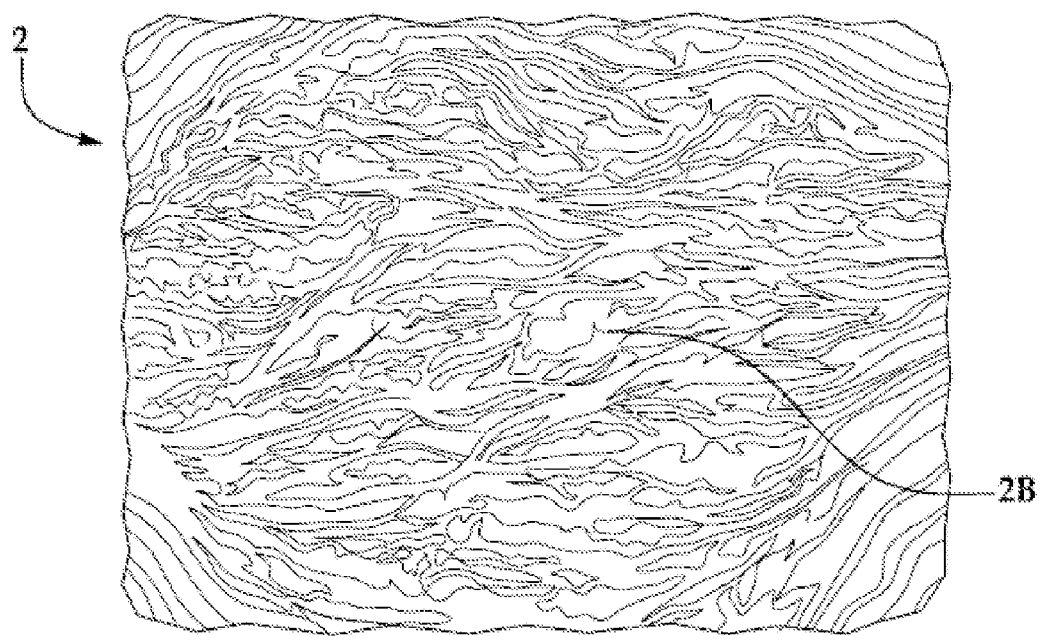
FIG. 1D illustrates another histology image of the cornea of FIG. 1A.

As further illustrated in FIGS. 1A and 1B, the changes in corneal structure are localized and limited to an area and a depth specifically determined by the controlled application of heat. FIGS. 1C and 1D illustrate histology images in which the tissue shown in FIGS. 1A and 1B has been stained to highlight the structural changes induced by the heat. In particular, the difference between the structure of collagen fibrils in the mid-depth region 2B where heat has penetrated and the structure of collagen fibrils outside the region 2B is clearly visible. Thus, the collagen fibrils outside the region 2B remain generally unaffected by the application of heat, while the collagen fibrils inside the region 2B have been rearranged and formed new bonds to create completely different structures. In other words, unlike processes, such as orthokeratology, which compress areas of the cornea to reshape the cornea via mechanical deformation, the collagen fibrils in the region 2B are in an entirely new state. Treatment of the cornea produces structural changes to the stroma 2C, and the optomechanical properties of the cornea change under stress. Such changes include: straightening out the waviness of the collagen fibrils; slippage and rotation of individual lamellae; and breakdown of aggregated molecular superstructures into smaller units.

Although treatments, such thermokeratoplasty, may initially achieve desired reshaping of the cornea, the desired effects of reshaping the cornea may be mitigated or reversed at least partially if the collagen fibrils continue to change after the desired reshaping has been achieved. Therefore, aspects of the present invention provide approaches for preserving the desired corneal structure and shape that result from an eye therapy, such as thermokeratoplasty. In general, embodiments provide approaches for initiating molecular cross-linking of the corneal collagen to stabilize the corneal tissue and improve its biomechanical strength.

Figure 2A:
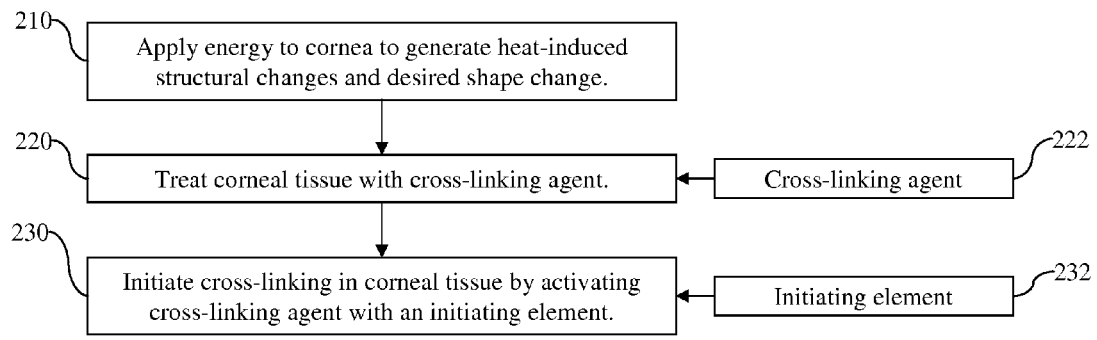
FIG. 2A illustrates an example approach for stabilizing or strengthening corneal tissue by applying a cross-linking agent according to aspects of the present invention.

Referring to FIG. 2A, a treatment, such as thermokeratoplasty or LASIK surgery, is applied in step 210 to generate structural changes in the cornea and produce a desired shape change. In step 220, the corneal tissue is treated with a cross-linking agent 222. The cross-linking agent may be applied directly on the treated tissue and/or in areas around the treated tissue. In some embodiments, the cross-linking agent may be an ophthalmic solution that is broadly delivered by a dropper, syringe, or the like. Alternatively, the cross-linking agent may be selectively applied as an ophthalmic ointment with an appropriate ointment applicator. The cross-linking agent 222 is then activated in step 230 with an initiating element 232. Activation of the cross-linking agent 222, for example, may be triggered thermally by the application of microwaves or light from a corresponding energy or light source. The resulting cross-linking between collagen fibrils provides resistance to changes in corneal structure.

As described previously with reference to FIGS. 1A-D, for example, the lesion 4 extends from the corneal surface 2A to a mid-depth region 2B in the corneal stroma 2C. In such cases, the application of the cross-linking agent in step 220 introduces sufficient amounts of cross-linking agent to mid-depth regions of the corneal tissue where stronger and more stable structure is desired.

Figure 2B:
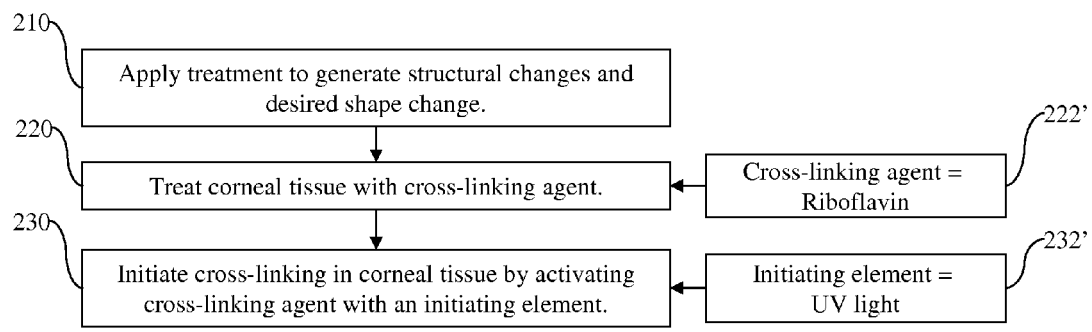
FIG. 2B illustrates an example approach for stabilizing or strengthening corneal tissue by applying Riboflavin as a cross-linking agent according to aspects of the present invention.

As FIG. 2B shows further, Ribloflavin is applied as a cross-linking agent 222' to the corneal tissue in step 220. In addition, light from a ultraviolet (UV) light source may be applied as an initiating element 232' in step 230 to initiate cross-linking in the corneal areas treated with Ribloflavin. Specifically, the UV light initiates cross-linking activity by causing the applied Riboflavin to release reactive oxygen radicals in the corneal tissue. The Riboflavin acts as a sensitizer to convert $O_2$ into singlet oxygen which causes cross-linking within the corneal tissue.

In human tissue, $O_2$ content is very low compared to the atmosphere. The rate of cross-linking in the cornea, however, is related to the concentration of $O_2$ when it is irradiated with photoactivating light. Therefore, it may be advantageous to increase or decrease the concentration of $O_2$ actively during irradiation to control the rate of cross-linking until a desired amount of cross-linking is achieved.

Figure 3A:
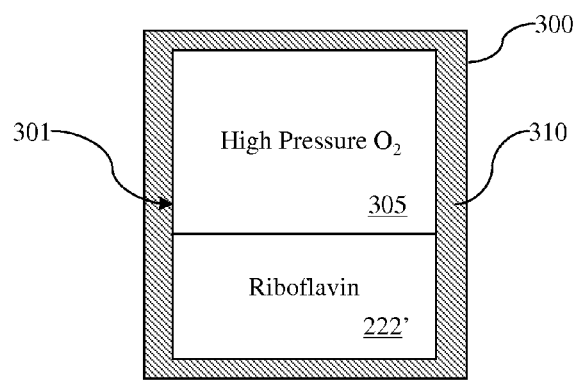
FIG. 3A illustrates an example device that may be employed to supersaturate a cross-linking agent with $O_2$ according to aspects of the present invention.
Figure 3B:
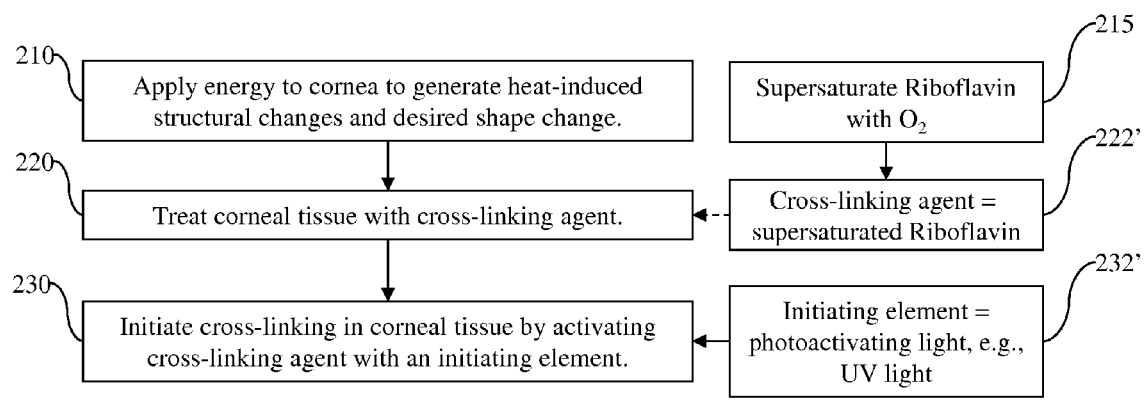
FIG. 3B illustrates an example approach for stabilizing or strengthening corneal tissue by applying supersaturated Riboflavin as a cross-linking agent according to aspects of the present invention.

An approach according to aspects of the present invention involves supersaturating the Riboflavin with $O_2$. Thus, when the Riboflavin is applied to the eye, a higher concentration of $O_2$ is delivered directly into the cornea with the Riboflavin and affects the conversion of $O_2$ into singlet oxygen when the Riboflavin is exposed to the photoactivating light. As illustrated in FIG. 3A, the Riboflavin 222' may be stored in a closed vessel, e.g., a vial, 300 under increased $O_2$ pressure 305. The increased $O_2$ pressure 305 results in a higher equilibrium concentration of $O_2$ in the Riboflavin 222'. The walls 310 of the vessel 300 are preferably opaque or otherwise prevent visible, UV, or other light from entering the vessel interior 301 to minimize the degradation of the Riboflavin 222'. Accordingly, referring to FIG. 3B, the step 215 supersaturates the Riboflavin 222' with $O_2$ so that a supersaturated Riboflavin 222' is applied in step 220.

Figure 4A:
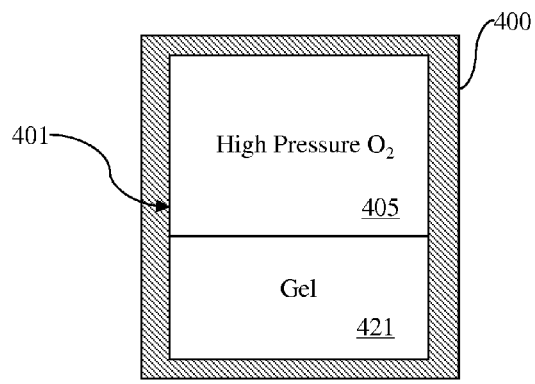
FIG. 4A illustrates an example device that may be employed to supersaturate a carrier gel with $O_2$ according to aspects of the present invention.

According to other aspects of the present invention, rather than supersaturating the Riboflavin 222' with $O_2$, another substance, such as a gel (e.g., a methylcellulose gel), may be saturated or supersaturated with $O_2$. As illustrated in FIG. 4A, a gel 421 may be stored in an interior 401 of a closed vessel, e.g., a vial, 400 under increased $O_2$ pressure 405. The increased $O_2$ pressure 405 results in a higher equilibrium concentration of $O_2$ in the gel 421. The gel can then act as a carrier for $O_2$.

Figure 4B:
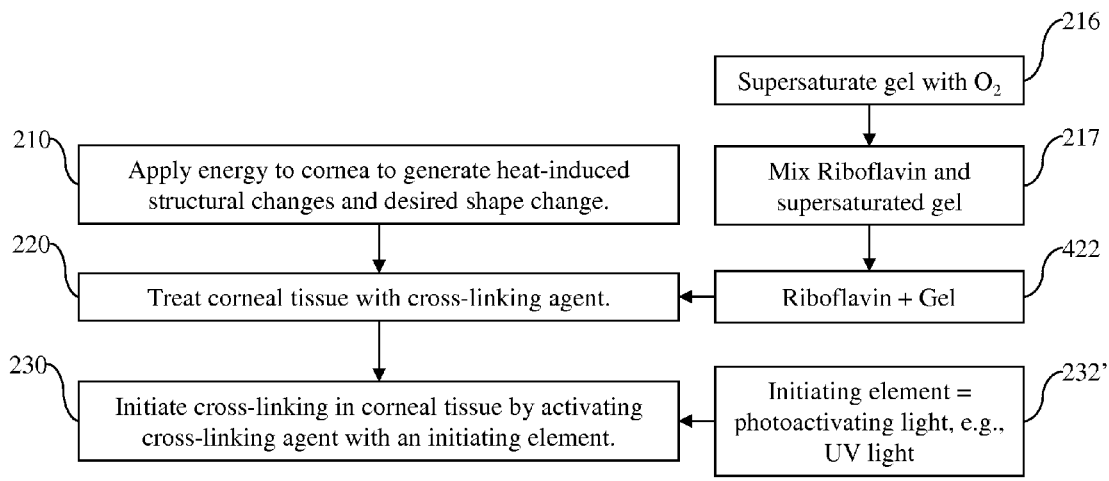
FIG. 4B illustrates an example approach for stabilizing or strengthening corneal tissue by mixing Riboflavin with a gel supersaturated with $O_2$ according to aspects of the present invention.
Figure 4C:
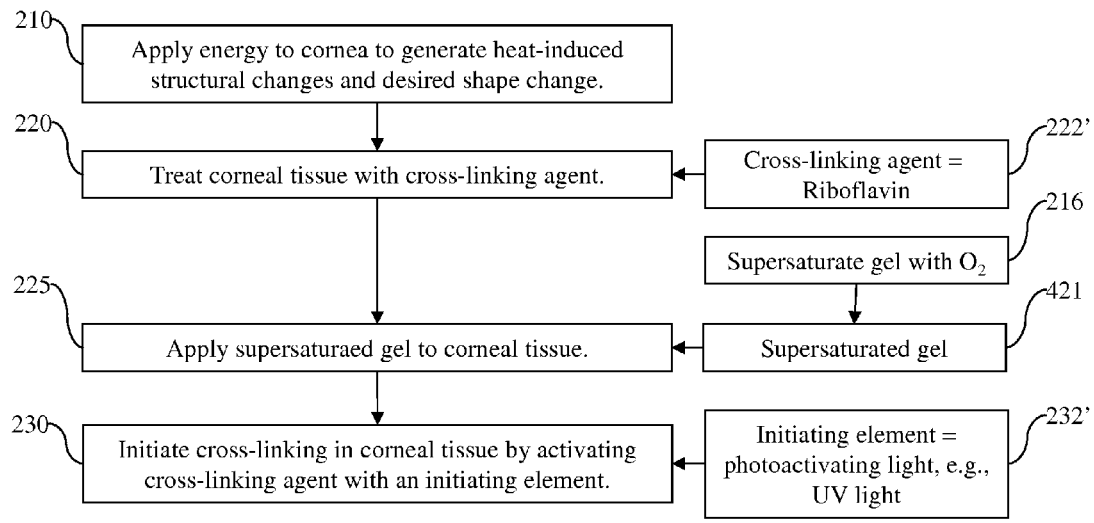
FIG. 4C illustrates an example approach for stabilizing or strengthening corneal tissue by applying a gel supersaturated with $O_2$ according to aspects of the present invention.

Referring to FIG. 4B, step 216 saturates a gel 421 with $O_2$, and step 217 mixes the supersaturated gel 421 with the Riboflavin 222', so that a mixture 422 containing the Riboflavin 222' and the supersaturated gel 421 is applied in step 220. Alternatively, referring to FIG. 4C, step 216 saturates a gel 421 with $O_2$, and step 225 applies the gel 421 to the cornea after the Riboflavin 222' has been applied to the cornea. In both FIGS. 4A and 4B, the gel 421 increases the presence of $O_2$ when the Riboflavin 222' is activated with the UV light.

According to additional aspects of the present invention, a steady state of $O_2$ may be maintained at the surface of the cornea to expose the cornea to a selected amount of $O_2$ and cause $O_2$ to enter the cornea. The photoactivating light can then be applied to a cornea with the desired $O_2$ content.

Figure 5A:
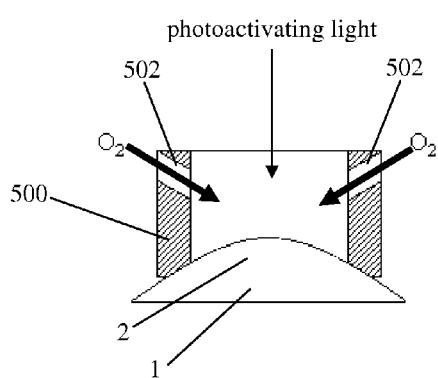
FIG. 5A illustrates an example device that may be employed maintain a steady state of $O_2$ above the eye to expose the cornea to higher concentrations of $O_2$ according to aspects of the present invention.

As shown in FIG. 5A, a ring 500 is placed on the eye 1 to supply $O_2$ to the cornea 2 during irradiation. The ring 500 includes one or more ports 502 that direct a steady flow of $O_2$ to the cornea 2, which has been treated by Riboflavin. The flow applies $O_2$ at high pressure against the cornea 2, so that more $O_2$ is available during the irradiation of the Riboflavin in the corneal tissue. The ring 500 may optionally be held in place by suction.

Figure 5B:
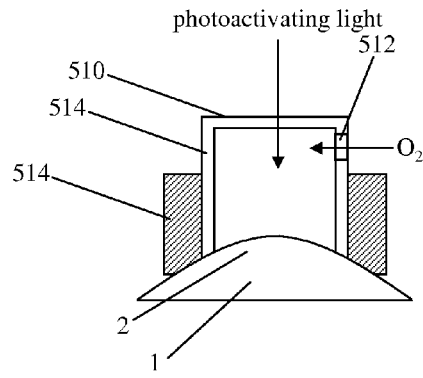
FIG. 5B illustrates another example device that may be employed to maintain a steady state of $O_2$ above the eye to expose the cornea to higher concentrations of $O_2$ according to aspects of the present invention.

As FIG. 5B illustrates, in another embodiment, an enclosure 510 receiving a supply of $O_2$ through a port 512 is placed on the eye to establish a steady state of $O_2$. The enclosure 510 may be held in place by a suction ring 512. As shown in FIG. 5B, the enclosure 510 may be a cup-like structure. The enclosure 510 maintains the $O_2$ at a higher pressure, e.g., higher than ambient, against the surface of the cornea 2. The concentration of $O_2$ within the enclosure 510 and above the surface of the cornea 2 can approach 100%. The $O_2$ within the enclosure 510 makes more $O_2$ to be available for the irradiation of the Riboflavin in the corneal tissue. At least a portion of the walls 514 of the enclosure 510 may be translucent to allow photoactivating light to pass through the enclosure 510 to irradiate the cornea 2 and activate the Riboflavin applied to the cornea 2. Alternatively, the light source may be disposed within the enclosure. The enclosure 510 may also include a valve that allows the gas to be released.

Figure 5C:
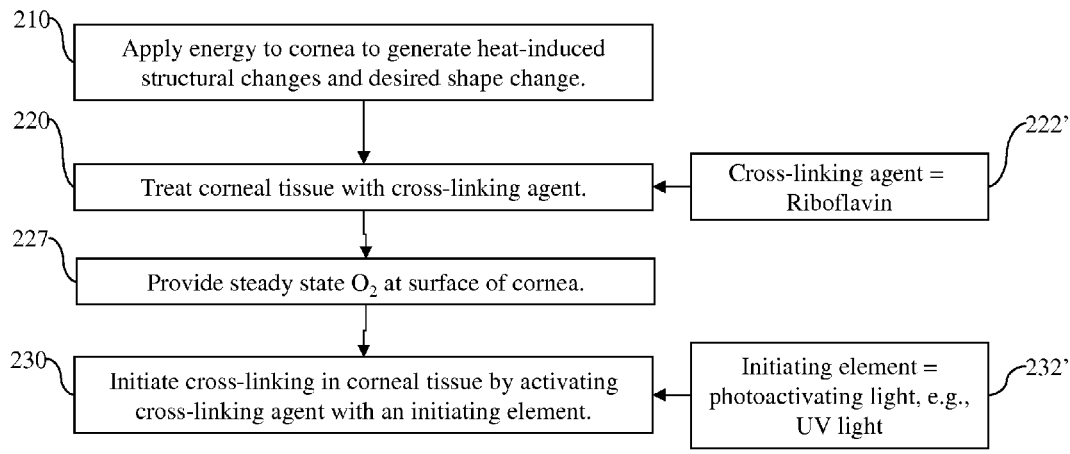
FIG. 5C illustrates an example approach for stabilizing or strengthening corneal tissue by applying a state of $O_2$ above the eye to expose the cornea to higher concentrations of $O_2$.

Accordingly, referring to FIG. 5C, step 227 establishes a steady state of $O_2$ above the corneal surface before the photoactivating light 232' is applied in step 230 to initiate cross-linking with the Riboflavin 222'.

Figure 6:
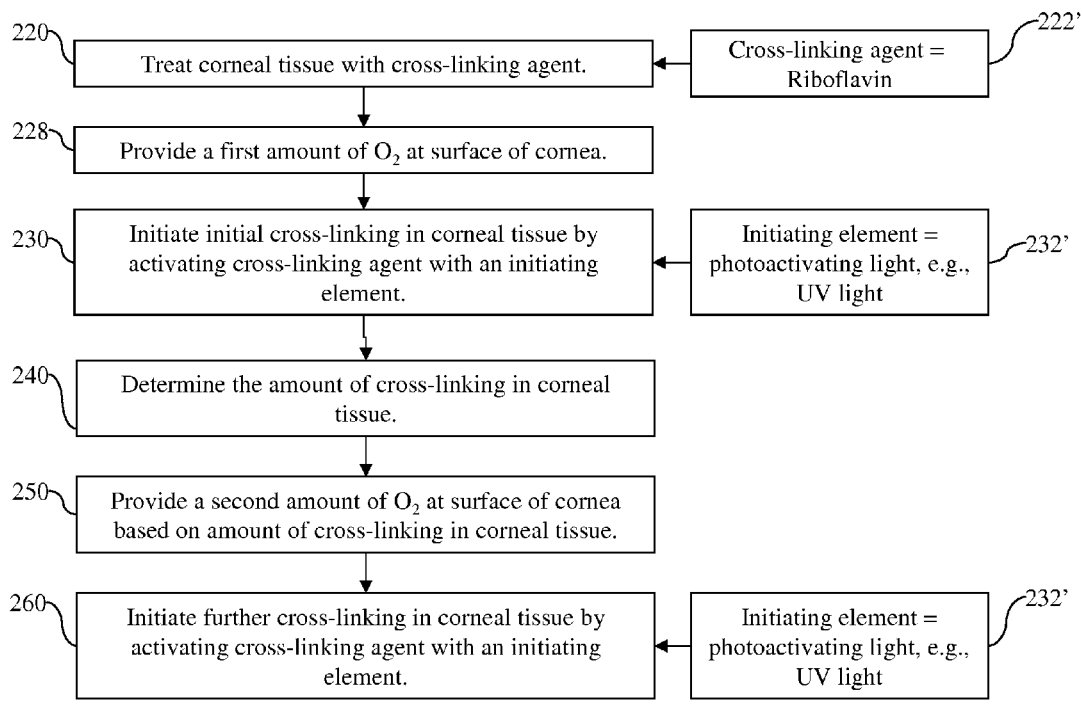
FIG. 6 illustrates an example approach for stabilizing or strengthening corneal tissue by monitoring cross-linking activity in real time and controlling the amount of $O_2$ exposure to achieve desired rates of cross-linking according to aspects of the present invention.

Referring to FIG. 6, the rate of cross-linking may be monitored in real time and the concentration of $O_2$ may be dynamically increased or decreased to achieve a desired amount of cross-linking. As FIG. 6 illustrates, corneal tissue is treated with Riboflavin 222' in step 220. In step 228, a first amount of $O_2$ is provided above the corneal surface to introduce $O_2$ to the corneal tissue and establish a first concentration of $O_2$ in the cornea during irradiation. The devices described with reference to FIGS. 5A and 5B may be employed to change the amount of $O_2$ is provided above the corneal surface. The Riboflavin 222' is then activated in step 230 with UV light 232'.

In step 240, the amount of cross-linking resulting from the activation of the Riboflavin 222' is monitored. One technique for monitoring the cross-linking employs polarimetry to measure corneal birefringence and to determine the structure of the corneal tissue. In particular, the technique measures the effects of cross-linking on corneal structure by applying polarized light to the corneal tissue. The corneal stroma is anisotropic and its index of refractions depends on direction. The cornea behaves like a curved biaxial crystal with the fast axis orthogonal to the corneal surface and the slow axis (or corneal polarization axis) tangential to the corneal surface. Accordingly, a light beam emerging from the living eye after a double pass through the ocular optics contains information on the polarization properties of the ocular structures (except optically inactive humours). The technique of using birefringence to monitor the structural changes resulting from cross-linking is described further in U.S. Provisional Patent Application No. 61/388,963, filed Oct. 1, 2010, the contents of which are entirely incorporated herein by reference. A controller, employing conventional computer hardware or similar processing hardware, can be used to monitor the amount of cross-linking. Such hardware may operate by reading and executing programmed instructions that are stored or fixed on computer-readable media, such as conventional computer disk. In addition to being coupled to monitoring hardware, the controller may be coupled to, and automatically control, the device(s) that provide the $O_2$ above the corneal surface.

Based on the information from the real time monitoring in step 240, step 250 provides a second amount of $O_2$ above the eye to introduce another amount of $O_2$ to the corneal tissue and expose the cornea to a second concentration of $O_2$ during irradiation with UV light 232' in step 260. Steps 240, 250, and 260 may be repeated any number of times to change the concentration of $O_2$ during irradiation to control the rate of cross-linking dynamically.

The first amount of $O_2$ in step 228 may be greater than the second amount of $O_2$ in step 250, or vice versa. Changing the cornea's exposure from the first concentration to the second concentration changes the rate of cross-linking in the corneal tissue as desired. If the information from step 240 indicates that the first amount of $O_2$ is too low, step 250 provides a second amount of $O_2$ that is greater than the first amount of $O_2$. On the other hand, if the information from step 240 indicates that the first amount of $O_2$ is too high, step 250 provides a second amount of $O_2$ that is greater than the first amount of $O_2$. It may be necessary to remove the first amount of $O_2$, e.g., from the enclosure 510, before providing the second amount of $O_2$ in step 250.

In some cases, it may be desired to provide substantially zero $O_2$ in step 250 to minimize or reduce the amount of $O_2$ in the corneal tissue during irradiation in step 260. Accordingly, step 250 may introduce a non-$O_2$ element or substance above the corneal surface. For example, nitrogen gas ($N_2$) may replace the $O_2$ supplied by the devices 500 and 510 shown in FIGS. 5A and 5B.

Although the embodiments described above may employ Riboflavin as a cross-linking agent, it is understood that other substances may be employed as a cross-linking agent. Thus, an embodiment may employ Rose Bengal (4,5,6,7-tetrachloro-2',4',5',7'-tetraiodofluorescein) as a cross-linking agent (similar to the embodiment of FIG. 3B). Rose Bengal has been approved for application to the eye as a stain to identify damage to conjunctival and corneal cells. However, Rose Bengal can also initiate cross-linking activity within corneal collagen to stabilize the corneal tissue and improve its biomechanical strength. Like Riboflavin, photoactivating light 332' may be applied to initiate cross-linking activity by causing the Rose Bengal to convert $O_2$ in the corneal tissue into singlet oxygen. The photoactivating light 332' may include, for example, UV light or green light.

Thus, with Rose Bengal, the rate of cross-linking in the cornea is related to the concentration of $O_2$ when it is irradiated with photoactivating light. Therefore, it may be advantageous to increase or decrease the concentration of $O_2$ during irradiation to control the rate of cross-linking and achieve the desired cross-linking. The concentration of $O_2$ may be increased or decreased according to the techniques described previously. For example, the Rose Bengal may be saturated or supersaturated with $O_2$ before application to the cornea. Additionally or alternatively, a steady state of $O_2$ may be maintained above the eye to expose the cornea to higher concentrations of $O_2$ and cause $O_2$ to enter the cornea. In general, the $O_2$ content in the cornea may be controlled for more effective cross-linking for any agent that operates to produce a reactive oxygen species for cross-linking.

Although aspects of the present invention have been described in connection with thermokeratoplasty or LASIK surgery, it is understood that the systems and methods described may be applied in other contexts. In other words, it may be advantageous to stabilize corneal structure with a cross-linking agent as described above as a part of any treatment.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention.

What is claimed is:

1. A system for controlling cross-linking in corneal tissue, comprising:
   a cross-linking system configured to apply a cross-linking agent to a cornea and activate the applied cross-linking agent to cause cross-linking in corneal fibrils of the cornea;
   a monitoring system configured to determine an amount of cross-linking in the cornea; and
   a delivery device configured to selectively adjust an $O_2$ content provided to the cornea to control the rate of cross-linking in response to the amount of cross-linking in the cornea determined by the monitoring system.

2. The system according to claim 1, wherein the delivery device is configured to provide a gas mixture that determines the $O_2$ content provided to the cornea.

3. The system according to claim 1, wherein the delivery device is configured to provide an oxygenated substance to the cornea, the oxygenated substance increasing the $O_2$ content in the corneal tissue when the oxygenated substance is applied.

4. The system according to claim 3, wherein the oxygenated substance includes Riboflavin.

5. The system according to claim 3, wherein the oxygenated substance includes a gel that is saturated or supersaturated with $O_2$.

6. The system according to claim 5, wherein the oxygenated substance includes the cross-linking agent and the gel.

7. The system according to claim 1, wherein the monitoring system is configured to determine the stiffness of the corneal tissue.

8. A system for controlling cross-linking in corneal tissue, comprising:
   a vessel that stores an oxygenated substance under $O_2$ pressure greater than ambient increasing the equilibrium concentration of $O_2$ for the oxygenated substance and causing the oxygenated substance to be saturated or supersaturated with $O_2$;
   a delivery device configured to apply the oxygenated substance to corneal fibrils in the corneal tissue, the oxygenated substance increasing the $O_2$ content in the corneal tissue when the oxygenated substance is applied; and
   a cross-linking system including a light source configured to activate a cross-linking agent applied to the corneal fibrils in the corneal tissue, the activated cross-linking agent causing cross-linking in the corneal fibrils.

9. The system according to claim 8, wherein the oxygenated substance includes a gel.

10. The system according to claim 8, wherein the oxygenated substance is mixed with the cross-linking agent before the oxygenated substance and the cross-linking agent are applied to the cornea.

11. The system according to claim 8, wherein the delivery device is configured to apply the oxygenated substance to the cornea before the cross-linking agent is applied to the cornea.

12. The system according to claim 11, further comprising an applicator configured to apply the cross-linking agent to the cornea.

13. The system according to claim 12, wherein the applicator is an eye dropper or a syringe.

14. The system according to claim 8, wherein the cross-linking agent is the oxygenated substance, the vessel storing the cross-linking agent under $O_2$ pressure greater than ambient that increases the equilibrium concentration of $O_2$ for the cross-linking agent causing the cross-linking agent to be saturated or supersaturated with $O_2$, the delivery device applying the cross-linking agent to the corneal fibrils.

15. A system for controlling cross-linking in corneal tissue, comprising:
   a cross-linking system configured to activate a cross-linking agent applied to a cornea to cause cross-linking in corneal fibrils of the cornea, the cross-linking system including a light source configured to direct a photoactivating light to the cornea; and
   a delivery device configured to selectively increase or decrease an $O_2$ content provided to the cornea to control the rate of cross-linking, wherein the delivery device is configured to selectively increase or decrease the $O_2$ content based on an assessment of the structure of the cornea.

16. The system according to claim 15, further comprising an applicator configured to apply the cross-linking agent to the cornea, the delivery device being configured to separately apply a gas mixture or an oxygenated substance to the cornea to control the rate of cross-linking.

17. The system according to claim 15, wherein the delivery device is configured to apply the cross-linking agent to the cornea, the cross-linking agent being saturated or supersaturated with $O_2$ such that the cross-linking agent increases the $O_2$ content in the cornea when the cross-linking agent is applied.

18. The system according to claim 17, wherein the delivery device is a syringe.

19. The system according to claim 15, wherein the delivery device is configured to apply a mixture of a cross-linking agent and an oxygenated substance to the cornea to increase the $O_2$ content in the cornea, the oxygenated substance being saturated or supersaturated with $O_2$.

20. The system according to claim 15, further comprising a monitoring system configured to provide the assessment of the structure of the cornea.

* * * * *